US010844141B2

(12) United States Patent
Araujo Rodrigues Muchiutti et al.

(10) Patent No.: US 10,844,141 B2
(45) Date of Patent: Nov. 24, 2020

(54) **PROCESS FOR OBTAINING POLYSACCHARIDES FROM JATOBA (*HYMENEA COURBARIL* L) SEEDS, COSMETIC COMPOSITION COMPRISING SAID POLYSACCHARIDES AND USES THEREOF**

(75) Inventors: Pamela Araujo Rodrigues Muchiutti, São André (BR); Cintia Rosa Ferrari, Carapicuiba (BR); César Gustavo Serafim Lisboa, São Bernardo (BR); Patrícia da Luz Moreira, São Paulo (BR); Kelen Fabiola Arroteia, Campinas (BR); Vanessa de Moura Sá Rocha, São Paulo (BR)

(73) Assignee: NATURA COSMÉTICOS S.A., Itapecerica da Serra (BR)

( * ) Notice: Subject to any disclaimer, the term of this patent is extended or adjusted under 35 U.S.C. 154(b) by 327 days.

(21) Appl. No.: 12/999,816

(22) PCT Filed: Jun. 19, 2009

(86) PCT No.: PCT/BR2009/000172
§ 371 (c)(1),
(2), (4) Date: Jun. 2, 2011

(87) PCT Pub. No.: WO2009/152595
PCT Pub. Date: Dec. 23, 2009

(65) Prior Publication Data
US 2012/0040926 A1  Feb. 16, 2012

(30) Foreign Application Priority Data
Jun. 19, 2008  (FR) .................................. 08 54067

(51) Int. Cl.
C08B 37/00 (2006.01)
C08B 37/18 (2006.01)
A61K 8/73 (2006.01)
A61Q 19/08 (2006.01)
A61K 8/9789 (2017.01)

(52) U.S. Cl.
CPC ............ *C08B 37/0003* (2013.01); *A61K 8/73* (2013.01); *A61K 8/9789* (2017.08); *A61Q 19/08* (2013.01); *C08B 37/006* (2013.01); *C08B 37/0024* (2013.01); *C08B 37/0057* (2013.01); *A61K 2800/48* (2013.01)

(58) Field of Classification Search
CPC ........... A61K 31/715; C07H 1/00; A61Q 1/00

USPC .................................. 536/124; 514/54, 844
See application file for complete search history.

(56) References Cited

U.S. PATENT DOCUMENTS 5,488,105 A    1/1996  Uno et al.
5,710,270 A *  1/1998  Maeda et al. ................. 536/124

FOREIGN PATENT DOCUMENTS

EP        0 965 321 A1      12/1999
JP        H10236943          9/1998
JP        2000-72649 A       3/2000
JP        2003-55190 A       2/2003
WO        WO 02/38273 A1 *   5/2002

OTHER PUBLICATIONS

Freitas et al., "Physico-Chemical Properties of Seed Xyloglucans from Different Sources," *Carbohydrate Polymers*, vol. 60, 2005, pp. 507-514.
Lima et al., "Oligosaccharides Derived from the Xyloglucan Isolated from the Seeds of *Hymenaea courbaril* var. *stilbocarpa*," *International Journal of Biological Macromolecules*, vol. 17, No. 6, 1995, pp. 413-415.
Martin et al., "Physico-Chemical Aspects of Galactoxyloglucan from the Seeds of *Hymenaea courbaril* and its Tetraborate Complex," *Carbohydrate Polymers*, vol. 54, 2003, pp. 287-295.
Tine et al., "Fine Structure of a Mixed-Oligomer Storage Xyloglucan from seeds of *Hymenaea courbaril*," *Carbohydrate Polymers*, vol. 66, 2006, pp. 444-454.
International Search Report and Written Opinion from corresponding International Appl. No. PCT/BR2009/000172, dated Aug. 20, 2009.
International Preliminary Report on Patentability from corresponding International Appl. No. PCT/BR2009/000172, dated Jul. 6, 2010.

* cited by examiner

*Primary Examiner* — Eric Olson
(74) *Attorney, Agent, or Firm* — Alston & Bird LLP (57) ABSTRACT

The present invention relates to a process for obtaining polysaccharides from jatoba seeds, comprising the steps of: a) seed processing (dry process); b) aqueous extraction at 1% to 5% of powder mass per volume, preferably 2% of powder mass per volume; c) precipitation with ethanol 969GL using 1 to 3 times the aqueous extract volume; d) press filtration of the precipitate obtained in (c); e) solubilization of the polysaccharides obtained in step (d) with water; and f) drying the polysaccharides obtained in step (e). In another embodiment, the present invention relates to a cosmetic composition containing polysaccharides obtained according to the process defined above and to the use of said polysaccharides.

2 Claims, 6 Drawing Sheets

PROCESS FOR OBTAINING POLYSACCHARIDES FROM JATOBA (*HYMENEA COURBARIL* L ) SEEDS, COSMETIC COMPOSITION COMPRISING SAID POLYSACCHARIDES AND USES THEREOF

FIELD OF THE INVENTION

The present invention relates to a process for obtaining polysaccharides, preferably xyloglucans, from jatoba seeds (*Hymenaea courbaril* L., *Hymenaea stilbocarpa*, among other species) to be applied in cosmetic compositions, preferably anti-aging compositions.

DESCRIPTION OF THE PRIOR ART

*Hymenaea courbaril* L., known as jatoba, is a tree originally found from Mexico to large part of South America, including Brazil (North to Southeast), Venezuela, Colombia, Peru and Bolivia. It is normally found in altitudes of up to 900 meters above sea level.

Its wood is used in civil engineering, woodwork, lathing, musical instruments and laminates, among others. The pulp is edible and is used in the preparation of food items, such as flours, sweets and drinks or in feedstuff. The bark and the sap of the trunk are used to prepare teas.

The xyloglucans are polysaccharides present on the cell wall of superior plants. The structural xyloglucan has the primary cell wall polysaccharide, and the xyloglucan obtained from seeds is predominantly a reserve polysaccharide. The main constituents of xyloglucan are galactose, glucose and xylose. In Brazil, jatoba (*Hymenaea courbaril*) seeds are an abundant source of xyloglucans. Xyloglucans act as active ingredients when applied to human skin, promoting benefits to general skin appearance and "health", stimutating the synthesis of collagen and elastin by connective cells.

U.S. Pat. No. 5,488,105 describes polysaccharides extracted from seeds of *Hymenaea* that are used as thickeners, gelatinizers and stabilizers in the formulation of food items, chemicals and pharmaceuticals. It also describes a process for extracting *Hymenaea* seeds including the steps of leaving the seeds to soak and removing the seed coats; grinding and drying the seeds to form a crude polysaccharide powder; suspending and filtering off the crude polysaccharide in an alkaline-alcohol solution and forming a purified polysaccharide; the purified polysaccharide is then dried and ground to form a purified polysaccharide powder.

Document JP 10236943 discloses the active ingredient of a cosmetic that is dissolved in an extract of jatoba. The extraction process is carried out with a non-aqueous solvent and fractionation.

From the description of the present invention below, it is concluded that the prior-art documents do not propose advantages in the sense of a simpler and cleaner process, that is to say, an ecologically correct process having a lower cost in relation to the prior-art processes.

SUMMARY OF THE INVENTION

The present invention relates to a process for obtaining polysaccharides from jatoba seeds, comprising the steps of:
a) seed processing (dry process);
b) aqueous extraction at 1% to 5% of powder mass per volume, preferably 2% of powder mass per volume;
c) precipitation with ethanol 96° GL using 1 to 3 times the aqueous extract volume;
d) press filtration of the precipitate obtained in (c);
e) solublization of the polysaccharides obtained in step (d) with water; and
f) drying the polysaccharides obtained in step (e).

DETAILED DESCRIPTION OF THE INVENTION

The object of the present invention is a process for obtaining polysaccharides from jatoba (*Hymenaea courbaril*) seeds.

One of the advantages of the present invention is that the process uses a simple and clean route, not involving the purification of crude polysaccharide with an alkaline-alcohol (NaOH) solution.

Another important aspect of the process of the present invention is the initial step of processing the seeds. It has been noticed that the use of water for washing the seeds negatively affects the result of the process since it causes a migration of some coat components to the inner part of the seed, thus resulting in a modification of the final product color in addition to a contamination and the presence of impurities.

More particularly, the present invention relates to a process for obtaining polysaccharides, preferably xyloglucans, from jatoba (*Hymenaea courbaril*) seeds comprising the steps of: seed processing, aqueous extraction at 1% to 5%, preferably at 2%; precipitation with ethanol 96° GL of 1 to 3 times the volume of the aqueous extract; solublization of the obtained polysaccharides with water and drying subsequently drying same.

The process starts with the processing of the seeds. In this step the seed coats are removed, which removal can be carried in two ways:

1) the intact seeds are ground and sieved for separating them from the seed coats. In a preferred embodiment of the present invention, grinding is done in hammer mill during an exhaustive time and the ground seeds are passed through 9 mm sieves for separating them from the seed coats. The coatless seeds are then granulometrically separated by passing through sieves of different mesh sizes, preferably, 3.35 mm, 2.36 mm, 1.18 mm and 600 μm sieves, respectively.

The fractions from the 9 mm sieve are retained in the 3.35 mm and 2.36 mm sieves, totaling 54% of the seed mass that is completely coatless.

2) according to a preferred embodiment, removing the seeds coats by using microwaves.

After seed processing, the resulting powder is slowly added to water with the aids of a sieve. Then an aqueous extraction is performed at 1% to 5%, preferably at 2%, of powder mass per volume. Extraction is preferably carried out with the water preheated at a temperature varying from 60° to 80° C., more preferably 70° C. After preheating, stirring is performed during a period of about 1 hour. Then, cooling occurs preferably up to 40° C.

Optionally, the process may further comprise a separation step that is preferably carried out by centrifugation. Centrifugation is preferably performed at 4100 RPM for 15 minutes.

After extraction and, if applicable, centrifugation, the material is submitted to precipitation with ethanol 96° GL, from 1 to 3 times the volume, preferably 3 times the volume. The inventors have discovered that said precipitation with ethanol 96° GL enables two different polysaccharides to be obtained: GEL (a denser and more gelled precipitate) and SOB (a less dense and more fibrous polysaccharide). These polysaccharides have the same saccharide constitution (monomers—galactose, xylose and glycose), but different molecular weights.

Optionally, the process may further comprise, after the alcoholic precipitation, a separation step that is preferably a press filtration for compressing the resulting mass.

Then, the resulting polysaccharides are suspended in water until solubilization in a concentration of 2% wt/volume. Normally for achieving this solubilization 10 minutes in an industrial mixer. It can also be carried out in a high shear grinder until the complete dispersion of the solid matter.

After solubilization, a separation is performed preferably through centrifugation, which is preferably done at 4100 RPM for 15 minutes. After separation, the supernatant is dehydrated by spray drying or freezing and subsequent freeze drying. In the case of freeze drying, it is necessary also to effect a grinding step.

In a preferred embodiment, the present invention refers to a process for obtaining xyloglucans from jatoba (*Hymenaea courbaril*) seeds comprising the steps of:

a) seed processing by drying the seeds in a microwave oven;
b) aqueous extraction at 2% at a temperature in a range of 60 to 80° C. for 1 hour
c) centrifugation at 4100 RPM for 15 minutes;
d) filtration (with granulometry in mycrosize) in a bowl with sheet;
e) precipitation with ethanol 96° GL at 1 to 3 times the volume;
f) solubilization of the obtained polysaccharides in water;
g) drying by spray drying or freezing and freeze-drying.

In another embodiment of the present invention, compositions comprising the polysaccharides obtained according to the process of the invention are provided in combination with cosmetically acceptable excipients. Those polysaccharides can be advantageous used, for example, for preparing ring anti-wrinkles or anti-age compositions and also as thickening agents in cosmetic formulations.

The table below illustrates some cosmetic compositions comprising xyloglucanes obtained in accordance with the process of the present invention:

| Process Phase | Components | Example 1 (%) | Example 2 (%) | Example 3 (%) |
|---|---|---|---|---|
| 1 | Demineralized water | 76.580 | 83.070 | 83.500 |
| 2 | Disodium EDTA | 0.100 | 0.100 | 0.100 |
| 3 | Bidistilled Glycerin BXR Vegetable | 5.000 | 5.000 | 5.000 |
| 4 | Xanthan Gum | — | 0.100 | 0.100 |
| 5 | Carbopol ETD 2020 | 0.250 | 0.180 | — |
| 6 | Cetyl alcohol | 1.000 | 3.000 | 2.000 |
| 6 | Stearyl alcohol | 1.000 | 1.000 | 2.000 |
| 7 | HYDROXYMETHYL ACRYLATE, SODIUM ACRYLOYLDIMETHYL TAURATE COPOLYMER AND SQUALANE AND POLYSORBATE 60 | 2.000 | 2.000 | 2.000 |
| 8 | Sodium Hydroxide | 0.070 | 0.050 | 0.050 |
| 9 | Demineralized water | 10.000 | 5.000 | 5.000 |
| 9 | Xyloglucan from *Jatoba* | 4.000 | 0.500 | 0.250 |
|   |   | 23.420 | 16.930 | 16.500 |

| Process Phase | Components | Example 4 (%) | Example 5 (%) | Example 6 (%) | Example 7 (%) |
|---|---|---|---|---|---|
| 1 | Demineralized water | 80.481 | 83.671 | 82.455 | 80.852 |
| 2 | Disodium EDTA | 0.100 | 0.100 | 0.100 | 0.100 |
| 3 | Bidistilled Glycerin BXR Vegetable | 5.000 | 5.000 | 5.000 | 5.000 |

-continued

| | | | | | |
|---|---|---|---|---|---|
| 4 | Xanthan Gum | 0.150 | 0.120 | 0.100 | 0.100 |
| 5 | Carbopol ETD 2020 | 0.210 | 0.250 | 0.300 | 0.100 |
| 6 | Cetyl alcohol | 0.500 | 2.300 | 1.500 | 4.000 |
| 6 | Stearyl alcohol | 2.500 | 1.200 | 1.500 | 2.000 |
| 7 | HYDROXYMETHYL ACRYLATE, SODIUM ACRYLOYLDIMETHYL TAURATE COPOLYMER AND SQUALANE AND POLYSORBATE 60 | 2.000 | 2.000 | 2.000 | 2.000 |
| 8 | Sodium Hydroxide | 0.059 | 0.059 | 0.045 | 0.048 |
| 9 | Demineralized water | 8.000 | 5.000 | 5.000 | 5.000 |
| 9 | Xyloglucan from *Jatoba* | 1.000 | 0.300 | 2.000 | 0.800 |
| | | 19.519 | 16.329 | 17.545 | 19.148 |

Process for Preparing the Compositions Described in the Table Above:

Pouring water into a container and weighing it (phase 1);
Adding the components indicated for phase 2 and stirring until complete solubilization;
Adding the components indicated for phase 3 and stirring;
Gradually adding the components indicated for phase 4 until complete solubilization; Strong stirring (approx. 1000 to 2000 rpm);
Gradually adding the ingredients of phase 5 with strong stirring until complete dispersion. It cannot form lumps.
Heating this phase up to 70-80° C.
In parallel, heating the components described for phase 6 at the same temperature.
With the components of phase 6 molten and at the same temperature as the aqueous phase, adding "phase 6" in aqueous phase and stirring at approx. 1000-2000 rpm.
Adding the components of phase 7 and strongly stirring until the formation of a smooth and bright emulsion in approx. 10-15 minutes.
In parallel to the beginning of the process, dispersing the polysaccharides in water, slowly adding it until complete solubilization.

This is a cooling phase, and the polysaccharides when contacted with other gums will promote synergy, with the formation of hydrogen bridges and change of the emulsion's viscoelastic/rheological properties.

Cosmetic Application

Some assays were carried out showing the enhanced and advantageous characteristics of the polysaccharides obtained in accordance with the process of the present invention for use in cosmetic compositions.

1) Cell Proliferation Activity:

Assays were carried out to assess the potential of the polysaccharides obtained in accordance with the present invention in promoting cell proliferation (the increase in the number of cells in relation to a control group not treated with the active ingredient) by analyzing cell viability through neutral red staining. Another object of the assays was to assess the procollagen potential of active ingredients (collagen in excess produced by the cells treated with the active ingredient in relation to the untreated control cells), by detecting the collagen in the culture supernatant through the sirius red stain.

The assay enables one to assess:

a) Whether or not the presence of a specific active ingredient in the cell culture, for one or more periods, results in an increase in the number of cells in relation to the control group (cells not treated with the same active ingredient). The number of cells is estimated as a function of the cell viability rate, which is monitored by the incubation of fibroblasts with the vital stain neutral red at the end of the assay period (96 h). This stain is incorporated into living cells so that the cell viability rate is given by the intensity of the stain absorbed by the cells in a directly proportional ratio. The colorimetric reading is carried out in a spectrophotometer, at the wavelength of 540 nm.

b) Whether or not the presence of the active ingredient induces the cells to produce more collagen per se. To this end, dermis-derived human fibroblasts are incubated with the tumor growth factor-$\beta$(TGF-$\beta$), known to induce collagen synthesis and secretion (positive control). Simultaneously, other fibroblasts under the same condition are incubated with the active ingredient being tested. The collagen is identified by the sirius red stain (picrosirius solution), which has affinity for procollagen and collagen molecules. The procollagen potential of each active ingredient is identified by the increase in optical density (absorbance 540 nm filter) measured after the dissolution of the pigments previously absorbed by the collagen present in the culture supernatants.

Results:

The results obtained with the polysaccharides produced according to the process of the present invention showed:

The proliferation/viability potential of the cells incubated with the different concentrations of the xyloglucan sample;
The procollagen potential of the active ingredient, normalized in function of the cell viability;
The total production of collagen, described in Tables 1 and 2.

TABLE 1

Cell proliferation (%), optical density (Abs) +/− standard deviation obtained from the reading of total collagen and collagen synthesis after normalization by the viability index (µg/ml and %), for human skin fibroblasts in primary culture, after 96 hours of incubation.

| Treatment | Cell Proliferation | Total Collagen ± standard deviation | Normalized Collagen (µg/ml) | Normalized Collagen (%) |
|---|---|---|---|---|
| Control | 100 | 0.152 ± 0.008 | 100.00 | 0.00 |
| TGF | 136.00 | 0.224 ± 0.009 | 198.10 | 98.10 |
| Batch 16 Xylo 0.01% | 108.57 | 0.236 ± 0.031 | 274.15 | 174.15 |
| Batch 16 Xylo 0.025% | 113.14 | 0.207 ± 0.001 | 202.76 | 102.76 |
| Batch 16 Xylo 0.05% | 113.14 | 0.21 ± 0.036 | 209.00 | 109.00 |
| Batch 16 Xylo 0.075% | 114.86 | 0.196 ± 0.025 | 177.20 | 77.20 |
| Batch 16 Xylo 0.1% | 115.43 | 0.173 ± 0.031 | 129.44 | 29.44 |

TABLE 2

Cell proliferation (%) and collagen synthesis after normalization
by the viability index (%), for human skin fibroblasts
in primary culture, after 96 hours of incubation with batches
780 and 781 (*jatoba* xyloglucans).

| Treatment | Cell Proliferation (%) | Collagen (%) |
|---|---|---|
| Control | 100.00 | 100.00 |
| TGF | 148.1 | 109.4 |
| Batch 780 - 0.1% | 109.3 | 266.0 |
| Batch 780 - 0.05% | 123.5 | 260.7 |
| Batch 781 - 0.01% | 146.6 | 164.8 |
| Batch 781 - 0.05% | 121.5 | 147.8 |

Regarding Cell Proliferation:

The incubation of the fibroblasts with the xyloglucan samples at the concentrations indicated above and in the conditions tested (96 hours) resulted in an increase in the amount of assay cells at all xyloglucan concentrations. Considering the results shown both in Tables 1 and 2 above, the lowest cell proliferation index was 8.6% at the lowest concentration tested (0.01%), while the highest proliferation index was 46.6%, with the xyloglucan sample at 0.01%.

Regarding the Synthesis of Collagen:

When applied at 0.01% for a period of 96 hours, the sample led to an increase of 174.15% in collagen synthesis. At the polysaccharide concentrations of 0.025 and 0.05%, the increase in the collagen synthesis was of 102 and 109%, respectively. These results are similar to the one found for the positive control of the assay (TGF-b, 98.1%) and significantly higher than for the baseline control of the assay (cells incubated only with culture medium).

At the two highest assay concentrations (0.075 and 0.1%), the levels of collagen increase were lower than those observed for the other concentrations of the sample (77.2 and 29.4%, respectively), but still significantly higher than for the negative control of the assay.

2) In Vitro Cell Senescence

The aim of this study was to assess the potential of the active ingredients in protecting the cell from cellular aging caused by sequential exposure to UVB radiation, using the b-galactosidase (liposome enzyme) senescence marker reduction parameter. This test can be used to assess whether the presence of active ingredients in human dermis fibroblasts can delay the increase in the expression of the b-galactosidase enzyme, which is associated with cells in a state of cellular senescence (aging). After thawing the cell batch, the cells are cultured in DMEM medium containing 10% SFB, in an atmosphere with 5% CO2, and at a temperature of 37° C. After plating, the cells are cultured in the same conditions for at least 48 hours.

After this period, one of the cell plates will be exposed to UVB radiation for 6 minutes, during 5 days (1 exposure per day), or during 4 days, and the other will be only incubated with buffer solution (PBS) for the same periods. The control group cells are treated only with PBS and culture medium; the treatment group is incubated with the active ingredient being tested, diluted in PBS (moment of exposure to radiation) or culture medium (intervals between the exposures to radiation). Once the exposure has been finished, the cells remain at rest for 48 to 72 hours (to consolidate the chronic effect resulting from the exposure to radiation), incubated in medium (control) or with the active ingredient diluted in medium (test group). After this period, the cells are exposed to the substrate from the b-galactosidase enzyme, which is converted into blue chromogen after 12 hours of incubation. Negative control cells have up to 10% positive b-galactosidade cells; positive control cells (exposed to UVB without the protection of the active ingredients) have from 45 to 65% positive b-galactosidade cells;

The method for obtaining the aging of human dermis fibroblasts in vitro was developed and validated by the Galápagos project (Funil de Tecnologia/Natura). However, the use of these cells in potential experimental applications (for example, assessment of the metabolic activity of senescent cells, reduction of senescence) has not yet been completely validated in the presence of control substances.

Results

Tables 3 and 4 indicates the percentage of positive b-galactosidase cells +/- the standard deviation of the percentage after each treatment with the samples containing xyloglucans obtained according to the present invention. UVB- refers to cells that were not exposed to the radiation and UVB+ refers to cells that were exposed to the radiation.

TABLE 3

|  | Treatment | Positive β-gal |
|---|---|---|
| UVB- | Control | 10.96 +/- 1.77 |
| UVB+ | C | 49.72 +/- 1.80 |
| UVB- | Xylo 12B | 11.25 +/- 0.2 |
| UVB+ |  | 39.55 +/- 2.06 |

TABLE 4

Trolox 0.005% is a substance used as positive control of the
test, since it prevents induced cellular senescence (about
30% senescent cells against about 50% untreated cells).

|  | Treatment | Positive β-gal |
|---|---|---|
| UVB- | Control | 11.67 +/- 1.05 |
|  | Trolox 0.005% | 11.33 +/- 1.39 |
|  | Xyloglucan 780 | 9.58 +/- 3.70 |
|  | Xyloglucan 781 | 8.67 +/- 1.39 |
| UVB+ | Control | 51.67 +/- 2.36 |
|  | Trolox 0.005% | 31.67 +/- 2.36 |
|  | Xyloglucan 780 | 27.26 +/- 1.40 |
|  | Xyloglucan 781 | 25.28 +/- 1.25 |

The assay results in Table 3 demonstrated that the presence of 0.01% xyloglucan resulted in a 10% reduction in the population of aged cells, recognized by the % of positive b-gal cells, after the period of fractionated exposure to UVB. The presence of the active ingredient protected the cells from damages caused by photoaging.

The assay results in Table 4 demonstrated that the presence of 0.025% xyloglucan resulted in a reduction in the population of aged cells, recognized by the positive b-gal cells, after the period of fractionated exposure to UVB. The presence of the active ingredient protected the cells from damages caused by photoaging.

Without incubating any samples (only in culture medium), the population of senescent cells corresponded to 51.67% of the total analyzed cells. In the presence of actives (780 and 781), the senescence index was 27.26% and 25.28%, respectively.

Both samples provided protection to induced photoaging. Cell morphology was better preserved in the presence of actives than in the absence thereof.

This data agrees with the information provided in preliminary report number 55, which showed the rate of 40% induced senescence when the cells were treated with xyloglucan (batch 0755507PI012B) at the concentration of 0.01%. The concentration tested in the present assay (0.025%) is 2.5 times higher than the one tested in the previous assay.

Conclusion:

In sum, it has been observed that xyloglucan has the ability to increase collagen synthesis, increase type I collagen gene expression, increase tropoelastin synthesis, and increase cell proliferation. Additionally, it protected the cells from cellular aging induced by prolonged exposure to UVB radiation in the cellular senescence model. All of these assays were carried out in cell culture, using human dermis fibroblasts.

| Benefit | Concentration tested | % increase | In vitro report |
|---|---|---|---|
| Cell proliferation | 0.05% | 15 | 24/08 |
| Collagen | 0.01%-0.1% | 40-80 | 24/08 |
| Type I collagen gene expression | 0.05% | 75% | — |
| Tropoelastin production | 0.01% | 68% | — |
| Cellular senescence | 0.01% | 10% | 55/08 |

Figure 1:
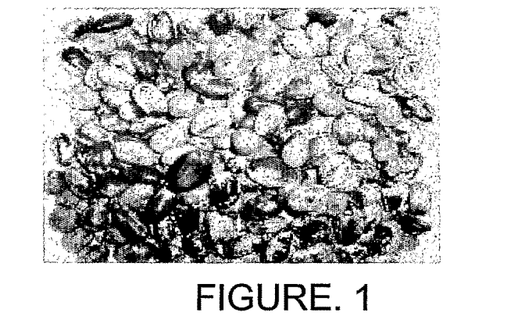
FIG. 1 shows *Hymenaea courbaril* seeds with coats.
Figure 2:
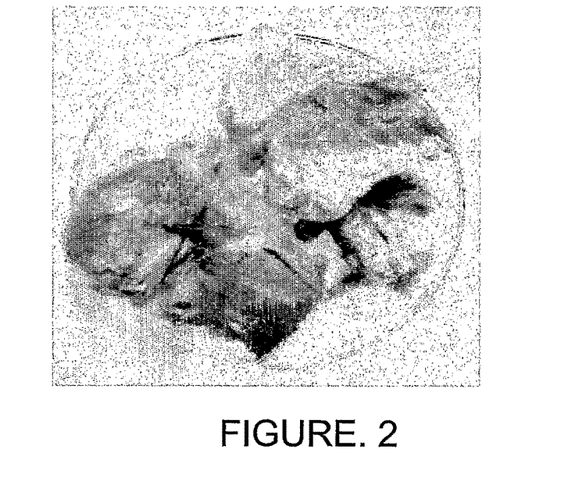
FIG. 2 illustrates a purified xyloglucan.
Figure 3:
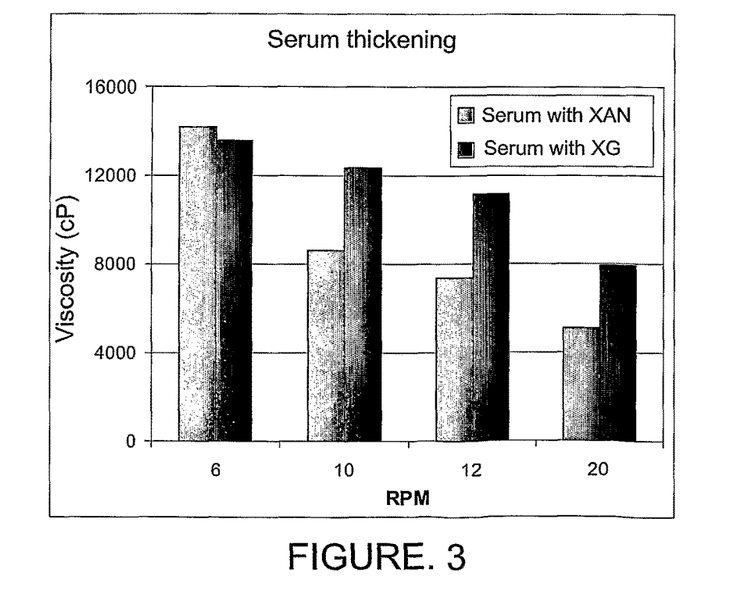
FIG. 3 shows a graph with results of the thickening activity of the polysaccharides obtained in accordance with the present invention.
Figure 4:
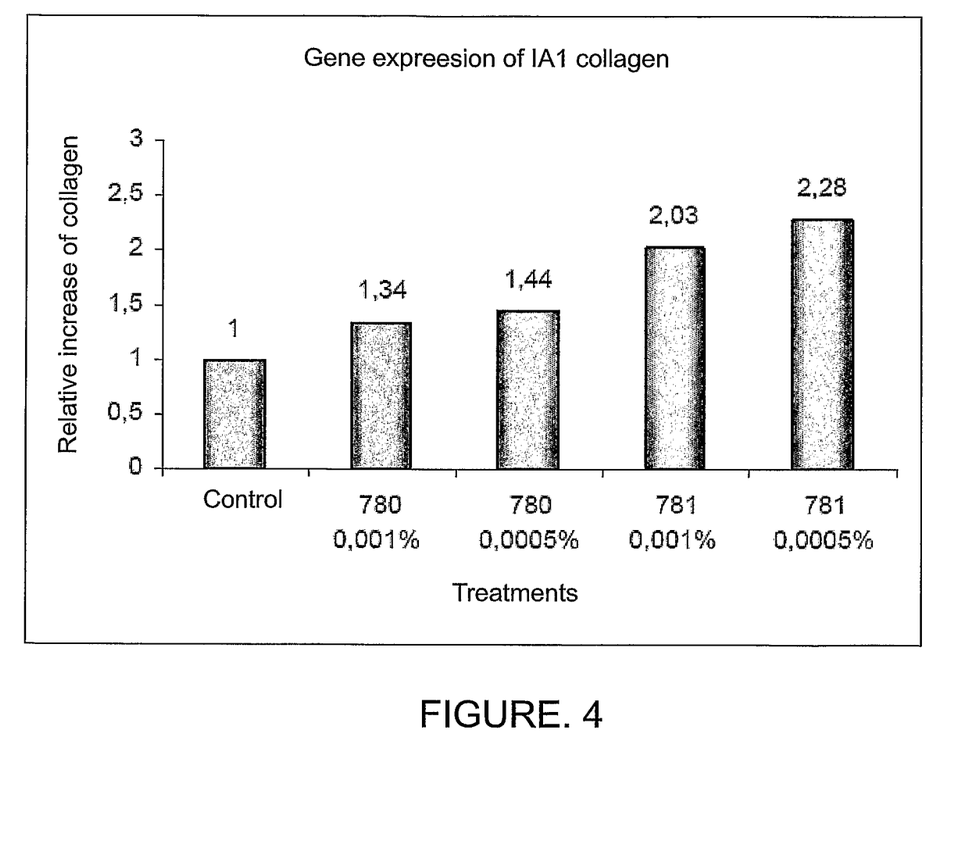
FIG. 4 shows the analysis of the relative expression of type I collagen in fibroblasts. Comparison with the control and treatment with different concentrations of samples 780 and 781 of xyloglucan.
Figure 5:
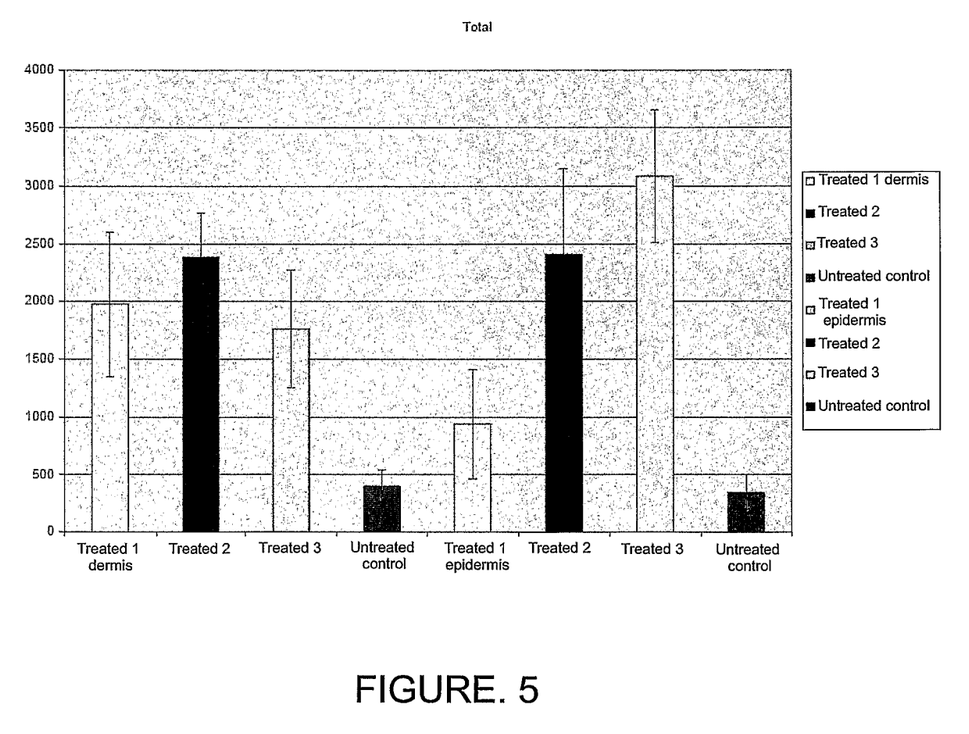
FIG. 5 shows the results obtained in the fluorescence reading obtained with calcofluor white staining of the histological sections made in skins submitted to cutaneous permeation with jatoba xyloglucan and the control. The readings were carried out separately in the dermis and epidermis. Skins 1 to 3 are the ones on which the jatoba xyloglucans were applied, and skin 4 is the control.
Figure 6:
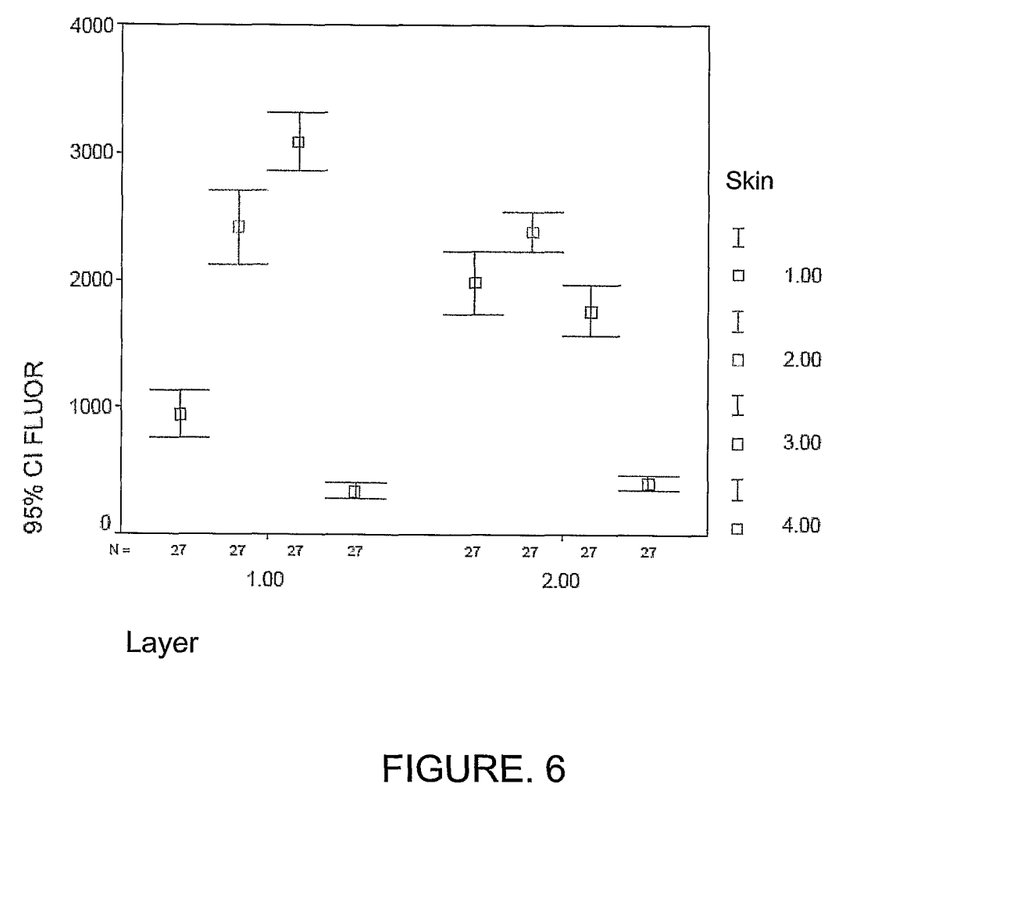
FIG. 6 shows the Fluorescence Intensity found in the dermis and epidermis after calcofluor staining. Layer 1 relates to the epidermis and layer 2 relates to the dermis. Skins 1, 2 and 3 were submitted to cutaneous permeation with jatoba xyloglucan. Skin 4 was submitted to the control.
Figure 7:
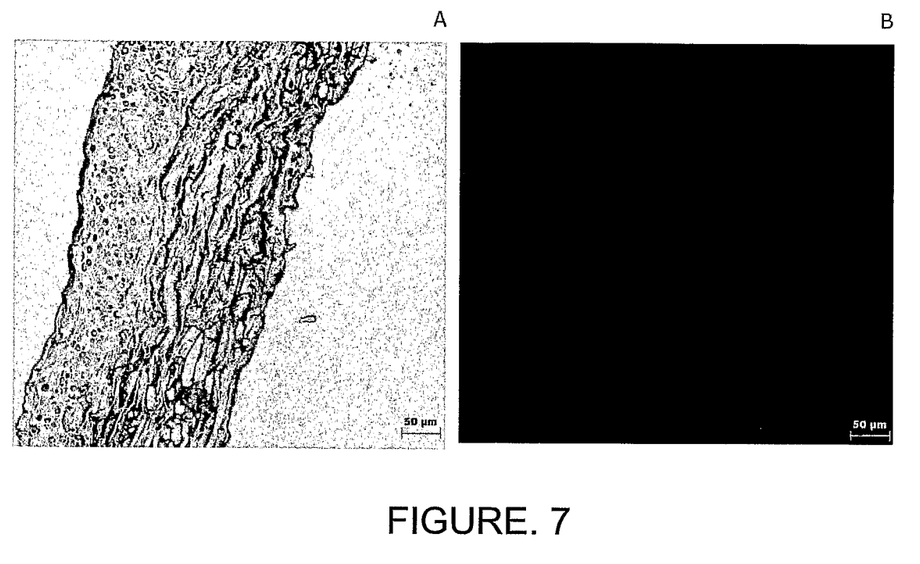
FIG. 7 shows the image obtained of the control skin without the treatment with calcofluor, in the light and dark fields of the microscope. The image shows that the skin alone does not emit fluorescence. A: light field; B: dark field.
Figure 8:
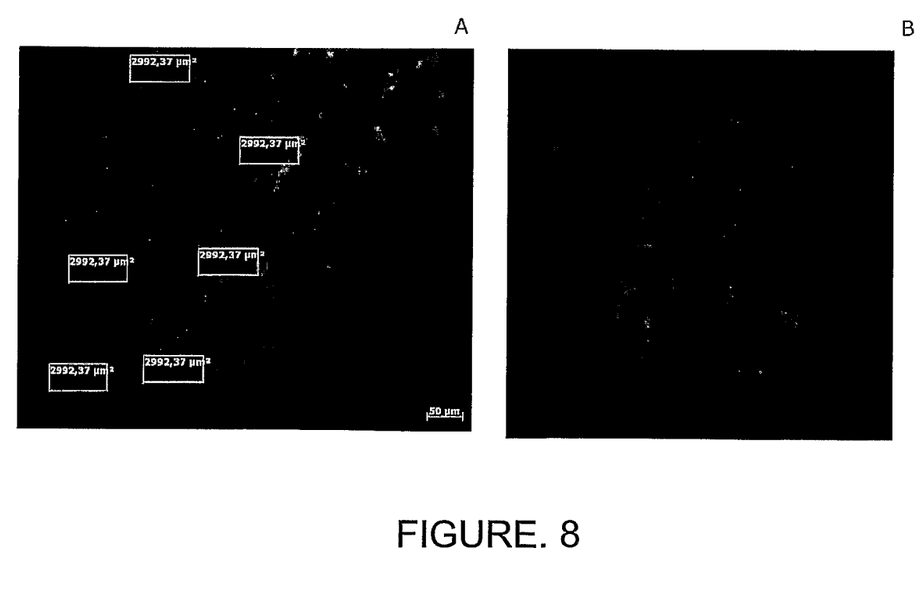
FIG. 8 shows the image obtained of the control skin fluorescence. Pictures of the histological section of the skin. A: Control skin, containing the area marked for fluorescence intensity measurement; B: Control skin without marking the area.
Figure 9:
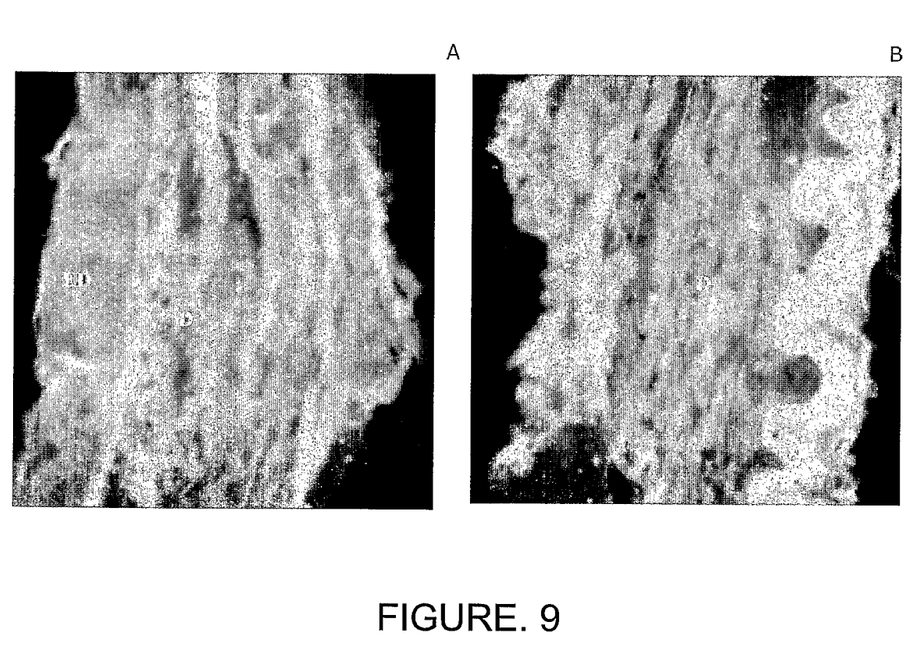
FIG. 9 shows the fluorescence after permeation with jatoba xyloglucan. Pictures of the histological section of the skin: ED—epidermis and D—dermis. A: Skin submitted to cutaneous permeation with jatoba xyloglucan for 24 h. ED and D show homogenous Fluorescence Intensity with calcofluor; B: Skin submitted to cutaneous permeation with jatoba xyloglucan for 24 h. ED shows greater Fluorescent Intensity than D in calcofluor staining.

In addition to the advantages described above, it was verified that the polysaccharides of the present invention can be used as thickening agents in cosmetic compositions. FIG. 3 contains a graph which shows the improved thickening activity of the polysaccharide of the present invention when compared to xanthan gum.

3) Collagen Gene Expression by Human Fibroblasts

The purpose of this assay is to assess the procollagen effect of extracts at non-cytotoxic concentrations, by relative quantification of type I collagen gene expression, using a culture of human skin fibroblasts.

One of the main characteristics of skin aging (either chronological or caused by exposure to UV rays, or by a combination of said factors) consists of the gradual loss of skin collagen content, especially type I collagens, the most abundant in the skin. The present methodology aims at determining botanical extracts with potential for stimulating the neosynthesis of collagen, and supplements data obtained from the methodology for assessing collagen secretion, leading to an increase in collagen gene expression, thereby closing the circuit—gene expression, production of collagen protein.

Human fibroblasts derived from the dermis are incubated with the tumor growth factor-β(TGF-β), which is a known inducer of the synthesis and secretion of collagen (positive control). Simultaneously, other fibroblasts in the same conditions are incubated with the active being tested. The incubation period is 24 hours. Then, the cell material was collected. For real-time PCR reactions, specific amplification systems for collagen I and also B2M (endogenous control) were used, in addition to Taqman Master Mix, from Applied Biosystems. The reactions were conducted on a thermocycler.

Results:

The results can be seen in Table 5.

Conclusion:

This assay indicated that jatoba xyloglucan has a procollagen potential of promoting an increase in type I collagen gene expression at the concentrations of 0.001% (10 ug/ml) and 0.0005% (5 ug/ml). Sample 781 had better performance in inducing type I collagen gene expression than sample 780. This data confirms previously obtained results for collagen secretion after the treatment of fibroblasts with the same active, suggesting that the active modulates collagen expression both transcriptionally and post-translationally.

3) In Vitro Permeation Assessment

In this assay, a semi-quantitative assessment of jatoba xyloglucan permeation was carried out by fluorescence microscopy with calcofluor white staining. Fluorescence is the result of a phenomenon in which fluorophore electrons absorb photons with ho energy from a source (a lamp or laser) and pass from a fundamental state (lower energy state) to an excited state (higher energy state). In this state, the fluorophore goes through a change in its conformation and can interact with a series of molecules surrounding it. Thus, the energy of this excited state is dissipated and the electron goes through a lower energy state, which is not necessarily the fundamental state. The energy difference between the excited state and the lower energy state is emitted in the form of a photon.

The following procedure is carried out in this assay:

Jatoba xyloglucan permeation for 24 h (3 Franz cells applying the xyloglucan solution at 2% and 1 Franz cell applying the PBS control).

Histological section by freezing. Thickness of the section: 10 μm. Skin fixed with meOH.

Staining performed with sol. Calcofluor in KOH 10% (1:1 v/v) for 1 min. Washing with water.

Reading in the fluorescence microscope with excitation at 400 nm

Number of readings/images captured: Three (3) different fields were captured for each slide section, both of the epidermis and of the dermis. Each slide had 3 histological sections. Total number of images=216.

Imaging software: Axiovision 4.6

Statistical analysis: Variance Analysis and Tukey's multiple comparison test.

Software for statistical analysis: SPSS

Results

The results are shown in FIGS. 5 to 9. In addition, the statistical analysis of the data was performed by ANOVA ("Analysis of Variance") and Tukey's Test, as seen in Tables 5 to 8 below. As the ANOVA statistical analysis indicated that there is a difference between the samples, that is, in the dermis or in the epidermis, without indicating which one is the different sample, a Tukey's test was carried out to check which samples are different.

TABLE 5

ANOVA statistical analysis for the epidermis
ANOVA$^a$
FLUOR

| | Sum of Squares | df | Mean Square | F | Sig. |
|---|---|---|---|---|---|
| Between Groups | 1.31E+08 | 3 | 43588451.65 | 154.643 | .000 |

TABLE 5-continued

ANOVA statistical analysis for the epidermis
ANOVA$^a$
FLUOR

|  | Sum of Squares | df | Mean Square | F | Sig. |
|---|---|---|---|---|---|
| Within Groups | 29314050 | 104 | 281865.866 | | |
| Total | 1.60E+08 | 107 | | | |

$^a$CAMADA = 1.00

TABLE 6

ANOVA statistical analysis for the dermis
ANOVA$^a$
FLUOR

|  | Sum of Squares | df | Mean Square | F | Sig. |
|---|---|---|---|---|---|
| Between Groups | 59739758 | 3 | 19913252.63 | 97.077 | .000 |
| Within Groups | 21333454 | 104 | 205129.367 | | |
| Total | 81073212 | 107 | | | |

$^a$CAMADA = 2.00

TABLE 7

Statistical analysis using Tukey's method (results for layer 1 - epidermis)
FLUOR$^b$
Tukey HSD$^a$

| | | Subset for alpha = .05 | | | |
|---|---|---|---|---|---|
| PELE | N | 1 | 2 | 3 | 4 |
| 4.00 | 27 | 340.7241 | | | |
| 1.00 | 27 | | 939.7807 | | |
| 2.00 | 27 | | | 2408.0067 | |
| 3.00 | 27 | | | | 3084.3689 |
| Sig. | | 1.000 | 1.000 | 1000 | 1.000 |

Means for groups in homogeneous subsets are displayed.
$^a$Uses Harmonic Mean Sample Size = 27.000.
$^b$CAMADA = 1.00

TABLE 8

Statistical analysis using Tukey's method (results for layer 2 - dermis)
FLUOR$^b$
Tukey HSD$^a$

| | | Subset for alpha = .05 | | |
|---|---|---|---|---|
| PELE | N | 1 | 2 | 3 |
| 4.00 | 27 | 401.7596 | | |
| 3.00 | 27 | | 1760.8648 | |
| 1.00 | 27 | | 1974.5856 | |
| 2.00 | 27 | | | 2383.7537 |
| Sig. | | 1.000 | .312 | 1.000 |

Means for groups in homogeneous subsets are displayed.
$^a$Uses Harmonic Mean Sample Size = 27.000.
$^b$CAMADA = 2.00

For the epidermis layer, the Tukey's Test indicated that all the skins had differences, while the control skin exhibited lower fluorescence (Table 7). For the dermis layer, all the skins treated with jatoba xyloglucan (1, 2 and 3) were different from the control (4). Skin 2 was different from skins 1 and 3 (Table 8).

Conclusion

The fluorescence microscopy technique used in this study is considered to be semi-quantitative, since no relationship is established between the Fluorescence Intensity and the concentration of jatoba xyloglucan in the skin. However, the fluorescence values measured increase in view of the concentration of jatoba xyloglucan, enabling one to infer whether xyloglucans are retained in the skin after the test. The results show that there is statistical evidence (Anova and Tukey) that the fluorescence intensity of the samples submitted to cutaneous permeation in vitro with jatoba xyloglucans is greater than the control (Anova and Tukey), indicating that the xyloglucan tested was retained in the treated skin. The statistical differences found between the treated skins reflect the variability of the test.

The invention claimed is:

1. A process for obtaining polysaccharides from jatoba (*Hymenaea courbaril*) seeds, the process consisting of:
   a) treatment of the seeds by using microwave for separating the coats;
   a1) grinding the treated seeds to obtain a powder;
   b) aqueous extraction at 1% to 5% of the powder mass per volume of the treated seeds obtained in step a) at a temperature of 70° C. for 4 hours;
   b1) separating the polysaccharides after the step of aqueous extraction, said separation being a centrifugation carried out at 4100 RPM for 15 minutes;
   c) precipitation with ethanol 96° GL using 1 to 3 times the aqueous extract volume;
   d) press filtration of the precipitate obtained in step (c);
   e) solubilization of the polysaccharides obtained in step (d) with water; and
   f) drying the polysaccharides obtained in step (e) by spray drying or by freeze drying,
   wherein the seeds obtained in step (a) are free from coat components in inner parts of the seeds.

2. The process of claim 1, wherein aqueous extraction in step (b) is performed at 2% powder mass per volume.

* * * * *